United States Patent
Tomaru

(10) Patent No.: US 8,502,970 B2
(45) Date of Patent: Aug. 6, 2013

(54) MICROSTRUCTURED BODY, PROCESS FOR PRODUCING THE MICROSTRUCTURED BODY, SENSOR DEVICE, AND RAMAN SPECTROMETRY DEVICE

(75) Inventor: Yuichi Tomaru, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 792 days.

(21) Appl. No.: 12/374,553

(22) PCT Filed: Jul. 11, 2007

(86) PCT No.: PCT/JP2007/063802
§ 371 (c)(1),
(2), (4) Date: Nov. 30, 2009

(87) PCT Pub. No.: WO2008/010442
PCT Pub. Date: Jan. 24, 2008

(65) Prior Publication Data
US 2010/0149530 A1    Jun. 17, 2010

(30) Foreign Application Priority Data
Jul. 20, 2006  (JP) .................................. 2006-198009

(51) Int. Cl.
*G01J 3/44* (2006.01)
(52) U.S. Cl.
USPC ........................................................ 356/301
(58) Field of Classification Search
USPC ....... 356/301, 244, 445; 427/383.7; 428/615
See application file for complete search history.

(56) References Cited

U.S. PATENT DOCUMENTS

| | | | |
|---|---|---|---|
| 7,158,219 B2 * | 1/2007 | Li et al. | ............................ 356/36 |
| 2005/0077184 A1 | 4/2005 | Lazarenko-Manevich et al. | |
| 2006/0181701 A1 | 8/2006 | Tomaru | |
| 2006/0280961 A1* | 12/2006 | Yamada et al. | ............... 428/671 |
| 2007/0285657 A1* | 12/2007 | Wang et al. | .................... 356/301 |

FOREIGN PATENT DOCUMENTS

| JP | 2004-170334 A | 6/2004 |
|---|---|---|
| JP | 2005-035564 A | 2/2005 |
| JP | 2005-171306 A | 6/2005 |
| JP | 2005-200677 A | 7/2005 |
| JP | 2006-038506 A | 2/2006 |
| JP | 2006-250924 A | 9/2006 |

OTHER PUBLICATIONS

CN First Office Action, dated Apr. 13, 2010, issued in corresponding CN Application No. 200780027434.9, 11 pages in English and Chinese.

* cited by examiner

Primary Examiner — Tarifur Chowdhury
Assistant Examiner — Abdullahi Nur
(74) Attorney, Agent, or Firm — Sughrue Mion, PLLC

(57) ABSTRACT

In order to simply produce a microstructured body in which metal particles are arranged so as to be fixed to depressions of a metal substrate having at a surface a structure of protrusions and the depressions, a process for producing the microstructured body includes the steps of: (A) preparing a metal substrate 11 with a surface having a structure of protrusions and depressions; (B) forming a metal film 21 on the surface of the metal substrate 11, where the metal film 21 contains as the main component a metal different from the constituent metal of the metal substrate 11; and (C) annealing the metal film so that the constituent metal of the metal film is coagulated into particles.

10 Claims, 5 Drawing Sheets

CONCRETE EXAMPLE 1 BEFORE ANNEALING

P=63nm

CONCRETE EXAMPLE 1 AFTER ANNEALING

P=63nm

CONCRETE EXAMPLE 2 BEFORE ANNEALING

P=100nm

CONCRETE EXAMPLE 2 AFTER ANNEALING

P=100nm

MICROSTRUCTURED BODY, PROCESS FOR PRODUCING THE MICROSTRUCTURED BODY, SENSOR DEVICE, AND RAMAN SPECTROMETRY DEVICE

BACKGROUND OF THE INVENTION

1. Field of the Invention

The present invention relates to a microstructured body in which metal particles are arranged on a metal substrate having a surface with a structure of protrusions and depressions. In addition, the present invention also relates to a process for producing the microstructured body. Further, the present invention relates to a sensor device using the microstructured body, and a device for Raman spectrometry (Raman spectrometry device) using the microstructured body.

2. Description of the Related Art

Sensor devices and Raman spectrometry devices which utilize localized plasmon resonance occurring at a metal surface are known. Raman spectrometry is a technique of obtaining a spectrum (Raman spectrum) of Raman scattered light which is obtained by irradiating a material with monochromatic light and splitting the scattered light into wavelength components. Since the Raman-scattered light is weak, a Raman spectrometry technique called surface-enhanced Raman scattering (SERS), in which an electric field enhanced by localized plasmon resonance is used for amplifying the weak Raman-scattered light, is known.

The localized plasmon resonance is a phenomenon in which a strong electric field is produced around a nano-order protrusion of a metal surface by vibration of free electrons in the nano-order protrusion in resonance with the electric field of light which is incident on the metal surface, where the metal surface has a structure of nano-order protrusions and nano-order depressions.

A microstructured body in which a great number of particles are fixed to a substrate and at least the surfaces of the particles are formed of metal has been proposed as a sensor device or Raman spectrometry device which utilizes the localized plasmon resonance.

The patent document 1 discloses a technique for producing a Raman spectrometry device having a particle layer constituted by a great number of nonmetal/metal composite particles regularly arranged on a substrate. According to the technique disclosed in the patent document 1, the particle layer is formed by regularly arranging a great number of nonmetal particles such as silica particles on a nonmetal substrate such as a glass substrate, and the substrate on which the particle layer is formed is immersed in a solution containing metal and a polymer. Thereafter, the particle layer is dried, and baked at a temperature at which the polymer can be burned off.

Patent Document 1: Japanese Unexamined Patent Publication No. 2004-170334
Patent Document 2: Japanese Patent Application No. 2005-035564
Patent Document 3: Japanese Unexamined Patent Publication No. 2005-200677
Patent Document 4: Japanese Unexamined Patent Publication No. 2006-038506

According to the technique disclosed in the patent document 1, the nonmetal particles are not fixed to the substrate in the stage in which the particle layer is formed. Therefore, although the nonmetal particles are not fixed to the substrate, it is necessary to perform the operations of immersing the substrate (on which the particle layer is formed) in the solution containing the metal and the polymer, and then taking the substrate out of the solution. Since the nonmetal particles are not fixed to the substrate, it is very difficult to perform the above operations so that the nonmetal particles do not drop off the substrate and the regular arrangement of the nonmetal particles is maintained.

The present inventor has performed research of a process for easily obtaining a microstructured body having a nano-order metal structure of protrusions and depressions, and has previously invented two types of Raman spectrometry devices (1) and (2). The Raman spectrometry device (1) is produced by anodizing a portion of a metal body (for example, of aluminum) so as to transform the portion into a layer of a metal oxide (e.g., $Al_2O_3$) and removing the layer of the metal oxide from the metal body, so that the Raman spectrometry device (1) is realized by the unanodized portion of the metal body. The Raman spectrometry device (2) is produced by fixing a metal substance to a surface of the above unanodized portion of the metal body by evaporation or the like, where the constituent metal of the metal substance fixed to the surface of the unanodized portion is different from the constituent metal of the metal body. Since the Raman scattering intensity is effectively enhanced in the Raman spectrometry device (2), the Raman spectrometry device (2) is particularly desirable. The Raman spectrometry devices (1) and (2) have been disclosed in the patent document 2 by the applicant of the present application, and the patent document 2 has not yet been laid open at the time of filing of the present patent application.

Since the unanodized portion of the metal body is a metal body with a surface having a nano-order metal structure of protrusions and depressions (for example, as illustrated in FIG. 2(c) in the patent document 2), the Raman spectrometry device can be easily produced by merely performing the operations of anodizing a metal body, removing the anodized portion of the metal body, and fixing a different metal to the unanodized portion of the metal body by evaporation or the like. In addition, since the anodization can produce an approximately regular structure, a Raman spectrometry device having a highly regular metal structure of protrusions and depressions can be easily produced.

In the Raman spectrometry device (2), the form of the metal substance fixed to the depressions of the unanodized portion of the metal body is not specifically limited. The metal substance fixed to the unanodized portion of the metal body is a metal film in the example disclosed in the patent document 2. (See FIG. 1(b) of the patent document 2.) The patent document 2 does not teach a technique for fixing metal particles to the depressions of the unanodized portion of the metal body.

The patent document 3 discloses a technique for producing metal particles by obtaining as a base an unanodized portion of a metal body, selectively precipitating metal particles in depressions of a surface of the base by use of a plating technique, and removing the base.

The patent document 4 discloses a technique for fixing, by use of metal colloid, metal particles to a surface of a microstructured body constituted by an unanodized portion and an anodized portion, where the surface has protrusions and depressions.

However, it is difficult to selectively fix metal particles to the depressions of the surface by the plating technique or the technique using metal colloid.

The patent document 3 reports that the technique for precipitating the metal particles by the plating technique requires a contrivance such as use of a special additive. (See paragraph 0025 in the patent document 3.)

In case where metal particles are fixed by use of metal colloid, the dimensions of the metal particles are known. Therefore, it is necessary to arrange the depressions so as to have dimensions corresponding to the dimensions of the metal particles. The patent document 4 discloses that the anodized portion is not removed, the metal particles are fixed to the surface of the anodized portion, and pore widening processing is performed for enlarging micropores in the anodized portion (which correspond to the depressions) according to the dimensions of the metal particles in the colloid. (See paragraphs 0064 to 0070 in the patent document 4.)

SUMMARY OF THE INVENTION

A first object of the present invention is to provide a process for easily producing a microstructured body on a metal substrate with a surface having a structure of protrusions and depressions, where a plurality of metal particles are fixed to and arranged in the depressions of the metal substrate.

A second object of the present invention is to provide a microstructured body produced by the above process.

A third object of the present invention is to provide a sensor device and a Raman spectrometry device which use the above microstructured body.

According to the first aspect of the present invention, there is provided a process for producing a microstructured body in which metal particles are arranged on a metal substrate. The process is characterized in comprising the steps of: (A) preparing the metal substrate with a surface having a structure of protrusions and depressions; (B) forming a metal film on the surface of the metal substrate, where the metal film contains as a main component a metal which is different from the constituent metal of the metal substrate; and (C) annealing the metal film so that the constituent metal of the metal film coagulates into particles.

In this specification, the "main component" means a component the content of which is 90 weight percent or more.

It is preferable that the annealing in step (C) be performed at a temperature equal to or higher than the melting point (melting temperature) of the metal film and lower than the melting point of the metal substrate.

In this specification, the "melting point of a metal film" means the melting point of a metal in the form of a film, and does not mean the melting point of the metal in bulk form. As explained later in detail, a phenomenon in which the melting point drops occurs in the structure according to the present invention. Specifically, the melting point of a metal film is lower than the melting point of the constituent metal of the metal film in bulk form.

It is preferable that the metal film formed in step (B) have a thickness greater than the depths of the depressions.

In this specification, the "thickness of a metal film" means the maximum thickness of the metal film.

According to the second aspect of the present invention, there is provided a microstructured body characterized in being produced by the process according to the first aspect of the present invention.

It is preferable that the depressions in the structure of the metal substrate have approximately identical shapes in a plan view, and be approximately regularly arranged in the structure of the metal substrate.

It is preferable that the average pitch between the depressions be equal to or smaller than 400 nm, which is smaller than the wavelength of the light applied for measurement in most cases.

In this specification, the expression "depressions . . . be approximately regularly arranged" means that the pitch between the depressions be approximately identical, and specifically the expression "the pitch between the depressions be approximately identical" means that the average pitch $P_{ave}$ between the depressions be within ±10%.

In a preferable example of the microstructured body according to the second aspect of the present invention, the metal substrate is produced by anodizing a portion of a metal body so as to produce a metal-oxide layer and removing the metal-oxide layer from the metal body so as to leave an unanodized portion of the metal body.

According to the third aspect of the present invention, there is provided a sensor device having a surface with which a specimen is to be arranged in contact, and outputting outgoing light with a physical property which is different according to the specimen and is to be detected when light for measurement is injected into the specimen. The sensor device according to the third aspect of the present invention is characterized in being realized by the microstructured body according to the second aspect of the present invention. The sensor device according to the third aspect of the present invention can perform sensing on the specimen by taking advantage of localized plasmon resonance which occurs at surfaces of the metal particles.

According to the fourth aspect of the present invention, there is provided a Raman spectrometry device having a surface with which a specimen is to be arranged in contact, and detecting Raman scattered light corresponding to light for measurement when the light for measurement is injected into the specimen. The Raman spectrometry device according to the fourth aspect of the present invention is characterized in being realized by the microstructured body according to the second aspect of the present invention.

Japanese Unexamined Patent Publication No. 10 (1998)-261224 (hereinafter referred to as JP10-261224A) discloses a technique for arranging metal particles on a dielectric substrate. In the technique disclosed in JP10-261224A, the dielectric substrate has at a surface a structure of protrusions and depressions, a metal film is formed on the dielectric substrate, and the metal film is annealed so that the constituent metal of the metal film is coagulated into particles. (See paragraph 0034.) That is, the formation of particles from a metal film by formation and annealing of the metal film on a nonmetal substrate having a structure of protrusions and depressions is conventionally known.

However, it has been conventionally considered that when a metal film is formed on a metal substrate, an alloy of the constituent metals of the metal substrate and the metal film is produced, and the constituent metal of the metal film is not formed into particles. Nevertheless, the present inventor has found that the melting point of a metal film formed on a metal substrate having a structure of protrusions and depressions drops, so that coagulation of the constituent metal of the metal film into particles can occur at a temperature far lower than the melting point of the bulk metal. Then, the present inventor has also found that even when a metal film is formed on a metal substrate having a structure of protrusions and depressions, the constituent metal of the metal film can be formed into particles without being transformed into an alloy. Then, the present inventor has also found that even when a metal film is formed on a metal substrate having a structure of protrusions and depressions, it is possible to transform the metal film into particles without producing an alloy, by using the phenomenon in which the melting point of the metal film formed on the metal substrate having the structure of protrusions and depressions drops. Thus, the present invention has been made.

Further, in the microstructured body according to the present invention, localized plasmon resonance also occurs at areas, to which no metal particles are fixed, of the surface of the metal substrate having a structure of protrusions and depressions. That is, localized plasmon resonance effectively occurs at both of the surface of the metal substrate and the surfaces of the metal particles, and it is possible to expect that interaction occurs between the localized plasmon resonance occurring at the surface of the metal substrate and the localized plasmon resonance occurring at the surfaces of the metal particles. Such advantages cannot be achieved by the technique disclosed in JP10-261224A.

The present invention has the following advantages.

As described before, in the process for producing a microstructured body according to the first aspect of the present invention, a metal substrate with a surface having a structure of protrusions and depressions is prepared in step (A), and a metal film containing as a main component a metal which is different from the constituent metal of the metal substrate is formed on the surface of the metal substrate in step (B). Then, the metal film is annealed in step (C) so that the constituent metal of the metal film is coagulated into particles. Therefore, when the metal film is annealed, the constituent metal of the metal film is automatically coagulated in the depressions of the metal substrate so that the constituent metal of the metal film is formed into particles. Thus, it is possible to selectively fix the metal particles in the depressions of the metal substrate by a simple process in which only the formation and annealing of a metal film are performed.

In addition, in the process for producing a microstructured body according to the first aspect of the present invention, each of the steps (from the step of forming the metal film to the final step of obtaining the microstructured body in which the metal particles are fixed in the depressions) is performed on the entire substrate by one operation. Therefore, even when the area of the substrate is large, the number of the steps is not changed, and the microstructured body can be produced by a very simple process. That is, the process for producing a microstructured body according to the first aspect of the present invention enables easy production of a microstructured body having a large area.

In the microstructured body produced by the process according to the first aspect of the present invention, localized plasmon resonance effectively occurs at both of the surface of the metal substrate and the surfaces of the metal particles, and interaction between the localized plasmon resonance occurring at the surface of the metal substrate and the localized plasmon resonance occurring at the surfaces of the metal particles is expected. Therefore, the microstructured body according to the second aspect of the present invention can be preferably used as sensor devices, Raman spectrometry devices, and the like which take advantage of localized plasmon resonance.

DETAILED DESCRIPTION OF THE INVENTION

Hereinbelow, details of the present invention are explained below.
1. MICROSTRUCTURED BODY A microstructured body according to an embodiment of the present invention is explained below with reference to drawings. FIG. 1 is a cross-sectional view along the thickness direction. FIGS. 2A to 2E are diagrams illustrating a production process, where FIGS. 2A and 2B are perspective views, and FIGS. 2C to 2E are cross-sectional views corresponding to FIG. 1.

As illustrated in FIG. 1, the microstructured body 1 according to the present embodiment is constituted by a metal substrate 11 and metal particles 20, where a surface of the metal substrate 11 has a structure of protrusions and depressions, and the metal particles 20 are arranged on the surface of the metal substrate 11. Specifically, a great number of dimples 12 are regularly arranged on the surface of the metal substrate 11 with an approximately constant pitch P, and the shapes of the dimples 12 are approximately identical in a plan view. More specifically, in a plan view, the dimples 12 have approximately equilateral hexagonal shapes, and are closely arranged without gaps so that six of the dimples 12 are arranged adjacent to each of the dimples 12 at the surface of the metal substrate 11. One of the metal particles 20 is fixed in each of the dimples 12 of the metal substrate 11.

The metal substrate 11 contains aluminum (Al) as a main component, and may contain inevitable impurities. As illustrated in FIGS. 2A to 2C, a metal body 10 is anodized so that a portion of the metal body 10 is transformed into an alumina ($Al_2O_3$) layer (metal-oxide layer) 30, and then the alumina layer 30 is removed. The remaining unanodized portion of the metal body 10 realizes the metal substrate 11. Although the thickness of the alumina layer 30, relative to the unanodized portion, is exaggeratedly illustrated for clarification in FIG. 2B, the thickness of the alumina layer 30, relative to the unanodized portion, is small in the actual process.

The shape of the metal body 10 is not specifically limited, and the metal body 10 may have a platelike shape. Further, the metal body 10 may be used with a support during the above process, for example, in case where the metal body 10 is a film formed on a support.

The anodization can be performed, for example, by immersing the metal body 10 and a cathode (as a counter electrode) in an electrolytic solution prepared for anodization, and applying a voltage between the cathode and the metal body 10, where the metal body 10 behaves as an anode, and the cathode is made of carbon, aluminum, or the like. The electrolytic solution is not specifically limited, and may be an acidic electrolytic solution containing one or more of sulfuric acid, phosphoric acid, chromic acid, oxalic acid, sulfamic acid, benzenesulfonic acid, and the like.

When anodization of the metal body 10 is performed, the anodization progresses from the surface 10s (the upper surface of the illustrated example) along the direction approximately perpendicular to the surface 10s, and the alumina layer 30 is produced as illustrated in FIG. 2B.

The alumina layer 30 produced by the anodization has a structure in which microcolumns 31 having approximately equilateral hexagonal shapes in a plan view are closely arranged. A micropore 32 extending from the surface 10s in the depth direction is formed approximately at the center of each of the microcolumns 31, and each of the microcolumns 31 has a round bottom end as illustrated in FIG. 2B. Therefore, the dimples 12 as mentioned before are formed at the surface of the unanodized portion on the anodized side. The structure of the metal oxide produced by anodization are indicated, for example, by Hideki Masuda, "Preparation of Mesoporous Alumina by Anodization and Application of Mesoporous Alumina as Functional Material", Material Technology, Vol. 15, No. 10, p. 34, 1997.

In the metal substrate 11, the pitch between the microcolumns 31 constituting the alumina layer 30 is directly reflected in the pitch between the dimples 12, and the vertical dimensions of the round bottom ends of the microcolumns 31 correspond to the depths of the dimples 12. For example, the average pitch P between the dimples 12 is approximately 2×1.2 E nanometers, and the depths d of the dimples 12 are approximately 1.2 E nanometers, where E is the voltage applied in the anodization (as indicated in OYO BUTSURI, Vol. 72, No. 10, 2003).

Since the object of the normal anodization is formation of the alumina layer 30 having the micropore 32 (mesoporous alumina), in the normal anodization, it is necessary to continue the oxidation reaction until the alumina layer 30 has a thickness necessary for the use of the alumina layer 30. On the other hand, according to the present embodiment, the anodization is performed for formation of the dimples 12 on the unanodized portion of the metal body 10, and the alumina layer 30 produced by the anodization is removed. Therefore, it is sufficient to form the alumina layer 30 with a minimum thickness as long as the dimples 12 can be stably formed.

Therefore, it is sufficient to appropriately design the anodization condition so that the unanodized portion remains and the dimples 12 are stably formed at a surface of the unanodized portion. In case where the electrolytic solution is oxalic acid, a preferable example of a condition for obtaining an approximately regular structure is that the concentration of the electrolytic solution is 0.5 M, the temperature of the electrolytic solution is 15° C., and the applied voltage is 40 V. The alumina layer 30 can be formed to have an arbitrary thickness by varying the duration of the electrolytic reaction. As long as the thickness of the metal body 10 before anodization is greater than the thickness of the alumina layer 30 to be produced by the anodization, the unanodized portion remains, so that the metal substrate 11 can be obtained.

The manner of selectively removing the alumina layer 30 and leaving the unanodized portion of the metal body 10 is not specifically limited. For example, the alumina layer 30 can be removed by etching the metal body 10 by using an etchant solution which selectively dissolve alumina (e.g., a solution of chromic acid), or by applying a voltage between the metal body 10 and the counter electrode in the reverse direction after completion of the anodization.

As explained above, the microstructured body according to the present embodiment is produced by preparing (in step (A)) the metal substrate 11 with a surface having a structure of protrusions and depressions, forming (in step (B)) on the surface of the metal substrate the metal film 21 containing as a main component a metal which is different from the constituent metal of the metal substrate 11, and annealing (in step (C)) the metal film 21 so that the constituent metal of the metal film 21 is coagulated into particles.

Although the average pitch P between the dimples 12 of the metal substrate 11 is not specifically limited, it is preferable, from the viewpoint of sensitivity, that the average pitch P be smaller than the wavelength of light applied for measurement in case where the microstructured body is used in a sensor device or a Raman spectrometry device. Specifically, the average pitch P between the dimples 12 is preferably 400 nm or smaller, which is smaller than the wavelength of the light applied for measurement in most cases.

The localized plasmon resonance is a phenomenon in which free electrons in a protruded portion oscillate in resonance with the electric field of light so that a strong electric field is produced around the protruded portion. Therefore, the localized plasmon resonance can occur in any metal, and thus the main component of the metal film 21 (the metal particles 20) may be any metal different from the constituent metal of the metal substrate 11. However, gold (Au), silver (Ag), copper (Cu), platinum (Pt), nickel (Ni), titanium (Ti), and the like are particularly preferable for the metal film 21.

The manner of formation of the metal film 21 is not specifically limited. However, it is preferable that the metal film 21 be formed by a vapor phase technique such as vacuum evaporation, sputtering, CVD, laser evaporation, or cluster ion beam bombardment. Since the metal substrate 11 is electrically conductive, the metal film 21 can be formed on a surface of the metal substrate 11 by electroplating. Alternatively, the metal film 21 can also be formed by attaching a great number of metal particles to the surface of the metal substrate 11, and coagulating the metal particles by heating, where the metal particles are attached to the surface of the metal substrate 11 by applying to the surface of the metal substrate 11 metal colloid in which the metal particles are dispersed, and drying the applied metal colloid.

The metal film 21 may be formed at either normal temperature or raised temperature. The film-formation temperature is not specifically limited. The thickness dm of the metal film 21 is not specifically limited. However, when the thickness dm of the metal film 21 is too small, it is difficult to stably produce particles. It is preferable that the thickness dm of the metal film 21 be greater than the depths d of the dimples 12. For example, the depths d of the dimples 12 are preferably 5 to 250 nm.

On the other hand, when the thickness dm of the metal film 21 is too great, adjacent ones of the metal particles 20 can cohere, so that production of particles can become difficult. In order to discretely arrange adjacent ones of the metal particles 20 in the dimples 12, it is preferable that the thickness dm of the metal film 21 not exceed twice the depths d of the dimples 12.

Although the manner of the annealing of the metal film 21 is not specifically limited, the metal film 21 may be annealed by laser annealing, electron-beam annealing, flash-lamp annealing, thermal-radiation annealing using a heater, electric-furnace annealing, or the like.

The present inventor considers that according to the present embodiment, the constituent metal of the metal film 21 is once melted by annealing, and the melted metal automatically coagulates in the respective dimples 12 of the metal substrate 11 while the temperature falls, so that the metal particles are produced. Since, according to the present embodiment, the dimples 12 have the round shapes, the metal particles 20 are produced in approximately globular shapes along the shapes of the dimples 12.

The annealing temperature is not specifically limited as long as the constituent metal of the metal film 21 can coagulate into particles. However, the annealing temperature is preferably equal to or higher than the melting point of the metal film 21 and lower than the melting point of the metal substrate 11. In the annealing step, it is necessary to coagulate the constituent metal of the metal film 21 and produce the metal particles without melting the metal substrate 11. Therefore, the annealing temperature is required to be set in consideration of the melting points of the metal substrate 11 and the dimples 12.

Generally, the melting point of bulk metal is very high. For example, the melting point of bulk gold is approximately 1064° C. Gold is a material preferable for the metal film 21. On the other hand, the metal substrate 11 in the present embodiment is constituted of aluminum, and the melting point of bulk aluminum is approximately 660° C., which is lower than the melting point of bulk gold. According to the conventional knowledge of metal properties, it would be considered that aluminum melts before gold coagulates, or an alloy of aluminum and gold is produced. That is, production of the microstructured body according to the present embodiment would be considered to be impossible.

However, the present inventor has found that the melting point of the metal film 21 formed on the metal substrate 11 having a structure of protrusions and depressions drops, so that the constituent metal of the metal film 21 can coagulate into particles at a temperature far lower than the melting point of the bulk metal. Then, the present inventor has also found that even when the metal film 21 is formed on the metal substrate 11 having a structure of protrusions and depressions, it is possible to coagulate the constituent metal of the metal film 21 into metal particles without producing an alloy, by taking advantage of the phenomenon in which the melting point of the metal film 21 formed on the metal substrate 11 having the structure of protrusions and depressions drops. This phenomenon outstandingly occurs when the thickness dm of the metal film 21 is on the order of nanometers. For example, it has been reported that the melting point of a nanosized substance of gold drops to approximately 300° C. and the properties of the nanosized substance of gold greatly vary when the dimension of the nanosized substance of gold is reduced to 2 nm. (See "Progress in Nanoparticles and Ultrafine Particles—Invention of Fine Particles by Nanotechnology and Spread of Use—" issued by Toray Research Center Inc.)

The amount of the drop in the melting point varies with the main component and the thickness dm of the metal film 21. When the melting point of the metal substrate 11 and the actual melting point determined by the main component and the thickness dm of the metal film 21, it is possible to more appropriately set the annealing temperature. Specifically, it is preferable that the annealing temperature be equal to or higher than the melting point of the metal film 21 and lower than the melting point of the metal substrate 11 (which is equal to the melting point of the bulk substance of the same material as the metal substrate 11).

When the annealing is performed as explained above, it is possible to fix the metal particles 20 in the dimples 12 of the metal substrate 11 by one operation. According to the present embodiment, the dimensions (diameters), the shapes, and the fixed locations of the metal particles 20 are determined according to the dimples 12 of the metal substrate 11. The metal substrate 11 has the structure of protrusions and depressions, the dimples 12 have approximately identical cross-sectional shapes in a plan view and are regularly arranged with an approximately constant pitch P in the structure of the metal substrate 11, and the metal particles 20 are formed in the dimples 12. Therefore, the metal particles 20 have high uniformity and high regularity of arrangement.

The microstructured body 1 according to the present embodiment is produced by forming on the metal substrate 11 the metal film 21 (the main component of which is a metal different from the constituent metal of the metal substrate 11), and annealing the metal film 21 so that the constituent metal of the metal film 21 is coagulated into particles. In this process, the constituent metal of the metal film 21 automatically coagulate into particles in the dimples 12 of the metal substrate 11 by the annealing the metal film 21. Therefore, it is possible to selectively fix the metal particles in the dimples 12 of the metal substrate 11 by a simple process in which only the formation and annealing of the metal film 21 are performed.

In addition, in the process for producing the microstructured body 1, each of the steps (from the step of producing the metal substrate 11 to the final step of obtaining the microstructured body 1 in which the metal particles 20 are fixed in the dimples 12) is performed on the entire substrate by one operation. Therefore, even when the area of the metal substrate 11 is large, the number of the steps is not changed, and the microstructured body 1 can be produced by a very simple process. That is, the microstructured body 1 according to the present embodiment can be easy produced so as to have a large area.

In the microstructured body 1 according to the present embodiment, localized plasmon resonance effectively occurs at both of the surface of the metal substrate 11 and the surfaces of the metal particles 20 fixed to the metal substrate 11, and interaction between the localized plasmon resonance occurring at the surface of the metal substrate 11 and the localized plasmon resonance occurring at the surfaces of the metal particles 20 is expected. Therefore, the microstructured body 1 according to the present embodiment can be preferably used as sensor devices, Raman spectrometry devices, and the like which take advantage of localized plasmon resonance.

As mentioned before in the "Description of the Related Art," the present inventor has previously invented the Raman spectrometry device produced by fixing a metal substance to a surface of an unanodized portion of a metal body by evaporation or the like, where the constituent metal of the metal substance fixed to the surface of the unanodized portion is different from the constituent metal of the metal body, as disclosed in the patent document 2 (which has not yet been laid open at the time of filing of the present patent application). In addition, as mentioned before, the form of the metal substance fixed to the depressions of the unanodized portion of the metal body is not specifically limited in the above Raman spectrometry device, and the patent document 2 discloses a metal film as an example of the fixed metal.

However, localized plasmon resonance occurs more effectively in the structure in which the metal particles 20 are fixed to the dimples 12 than in the structure disclosed in the patent document 2 in which the metal film is formed over the metal substrate. Therefore, the fixing of the metal particles 20 is more preferable than the formation of the metal film as disclosed in the patent document 2. Specifically, the localized plasmon resonance is realized by vibration of electrons in the discrete metal particles, while the free electrons in the continuous metal film are confined and do not vibrate. Therefore, it is possible to consider that the fixing of the metal particles is structurally superior to the formation of the metal film in realization of localized plasmon resonance.

The microstructured body 1 according to the present embodiment is produced by use of the metal substrate 11 having the surface at which the dimples 12 having the approximately identical cross-sectional shapes in a plan view are formed by anodization and are regularly arranged with the approximately constant pitch P. Therefore, the dimples 12 and the metal particles 20 fixed to the dimples 12 are arranged with high uniformity and high regularity. Since the microstructured body 1 has the above structure which is approximately regular, the microstructured body 1 has high in-plane uniformity, and localized plasmon resonance occurs over the entire surface of the microstructured body 1. Thus, when the microstructured body 1 is used in a sensor device or Raman spectrometry device, it is possible to stably perform sensing or analysis. That is, the microstructured body 1 can be preferably used in a sensor device or Raman spectrometry device.

2. Examples of Variations

Although only aluminum is referred to as the main component of the metal body 10 in the above embodiment, the metal body 10 may be made of any material which can be anodized. Specifically, Ti, Ta, Hf, Zr, and the like are examples of the metal which can be anodized. The metal body 10 may contain two or more metals.

Although the regularity of the structure of the microstructured body 1 can be low according to the anodization condition, the microstructured body according to the present invention may be produced by use of a metal substrate having protrusions and depressions arranged with low regularity.

The metal substrate having a structure of protrusions and depressions may be formed by micromachining, instead of anodization. For example, the depressions may be formed by lithography of a surface of a flat metal substrate. Alternatively, the depressions may be drawn on a surface of a flat metal substrate by an electronic drawing technique such as focused-ion-beam (FIB) technique or an electron-beam (EB) technique. The depressions may or may not be regularly arranged. However, use of anodization enables processing of the entire surface by one operation, allows increase in the surface area of the microstructured body, and does not require expensive equipment. Therefore, the embodiment which is explained before and uses anodization is particularly preferable.

3. Concrete Examples

Concrete examples of the present invention are explained below.

3.1 Production Process

Each of the concrete examples 1 and 2 of the microstructured body 1 according to the embodiment of the present invention explained before has been produced as follows.

First, a plate of aluminum (with a purity of 99.99% and a thickness of 10 mm) is prepared as the metal body 10. Then, anodization of the Al plate has been performed under such a condition that a portion of the Al plate is transformed into an alumina layer 30. In the anodization, the above Al plate (which is to be anodized) behaves as the anode, the cathode has also been made of aluminum, and the temperature of the electrolyte has been 15° C. In addition, in the process for producing the concrete example 1, the electrolyte has been a 0.3M solution of sulfuric acid, the applied voltage has been 25 V, and the reaction time has been 8 hours. In the process for producing the concrete example 2, the electrolyte has been a 0.5M solution of oxalic acid, the applied voltage has been 40 V, and the reaction time has been 5 hours.

After the above reaction is completed in each of the processes for producing the concrete examples 1 and 2, the alumina layer 30 is removed by wet etching using a chromic/phosphoric acid solution, so that a metal substrate 11 being constituted by only the unanodized portion of the metal body 10 and having a structure of protrusions and depressions has been obtained.

The present inventor has observed the surfaces of the metal substrates 11 for the concrete examples 1 and 2 by scanning electron microscope (SEM), and has found that the surfaces have a structure in which the dimples 12 having approximately equilateral hexagonal shapes are regularly arranged in a plan view. The pitch P of the dimples 12 has been measured to be 63 nm in the concrete example 1, and approximately 100 nm in the concrete example 2. Although the depths d of the dimples 12 have not been measured, the depths d of the dimples 12 have been estimated to be approximately 5 to 30 nm in the concrete example 1, and approximately 5 to 50 nm in the concrete example 2.

Next, the surface of the metal substrate 11 obtained as above has been evaporated with gold by vacuum evaporation so as to form a metal film 21. The evaporation has been performed under such a condition that the entire surface of the metal substrate 11 is covered with gold as illustrated in FIG. 2D. FIGS. 3A and 4A are SEM micrographs of the surfaces of the metal substrates 11 in the concrete examples 1 and 2 after the evaporation.

Thereafter, the metal substrate 11 having the metal film 21 has been annealed at 500° C. in a muffle furnace for five minutes, and has been naturally cooled to room temperature. The present inventor has also observed the surfaces of the metal substrates 11 in the concrete examples 1 and 2 after the annealing by SEM, and confirmed that nanoparticles of gold are approximately regularly arranged and one of the Au nanoparticles is fixed in each of the dimples 12 as illustrated in FIG. 2E. That is, completion of the microstructured body 1 has been confirmed. FIGS. 3B and 4B are SEM micrographs of the surfaces of the concrete examples 1 and 2 after the annealing.

3.2 Evaluation

Raman spectrometry has been performed by using each of the concrete examples 1 and 2 of the microstructured body 1 as a Raman spectrometry device, where an identical specimen solution has been attached to the surfaces of the concrete examples 1 and 2.

In the Raman spectrometry, HR-800, available from Horiba, Ltd., has been used, and a laser with the excitation wavelength of 532 nm and the output power of 4.3 µw has been used as a light source. The specimen solution is a 2.6 mM solution of R6G (6-carboxyrhodamine). It is known that R6G exhibits a Raman spectrum having a peak around the wave number of 1360 cm$^{-1}$. FIGS. 5 and 6 show the Raman spectra obtained by use of the concrete examples 1 and 2, respectively, where the measurement wavelength is 532 nm.

As indicated in FIGS. 5 and 6, in each of the cases where the concrete examples 1 and 2 of the microstructured body 1 are used as Raman spectrometry devices, a peak has been observed at the wave number specific to R6G (at the wave number of 1360 cm$^{-1}$). That is, a Raman signal has been clearly detected. Thus, a great surface-enhanced Raman effect and effective localized plasmon resonance have been confirmed in cases where the microstructured body 1 is used as a Raman spectrometry device. In other words, the effectiveness of the present invention has been confirmed.

4. Industrial Usability

The microstructured body according to the present invention can be preferably used as a Raman spectrometry device or a sensor device for use in a biosensor.

Figure 1:
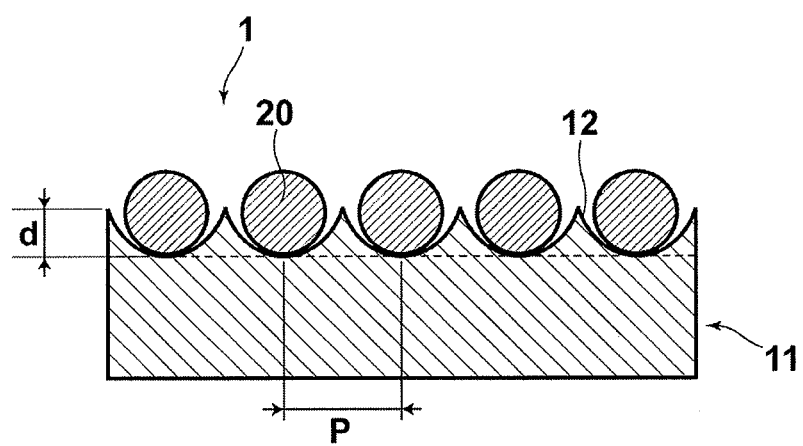
FIG. 1 is a diagram illustrating the structure of a microstructured body according to an embodiment of the present invention.
Figure 2A:
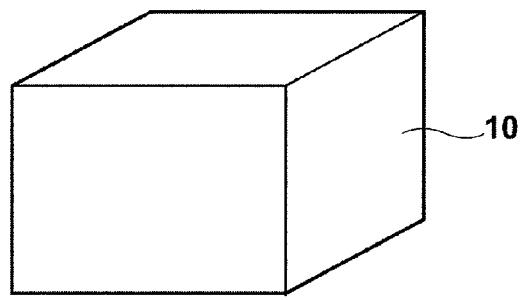
FIGS. 2A to 2E are diagrams illustrating a process for producing a microstructured body of FIG. 1.
Figure 2B:
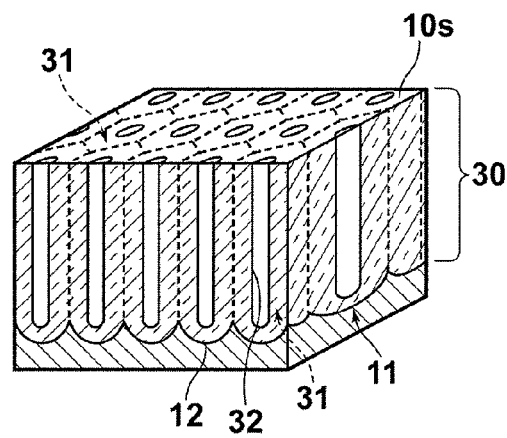
Figure 2C:
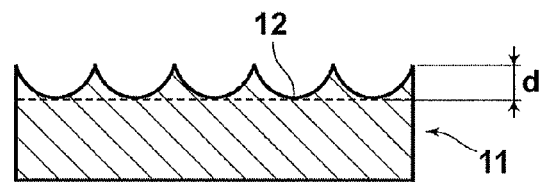
Figure 2D:
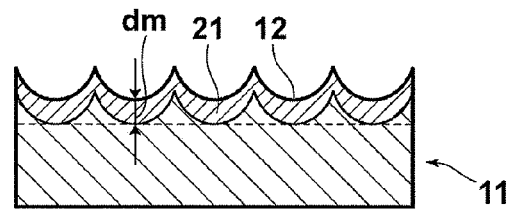
Figure 2E:
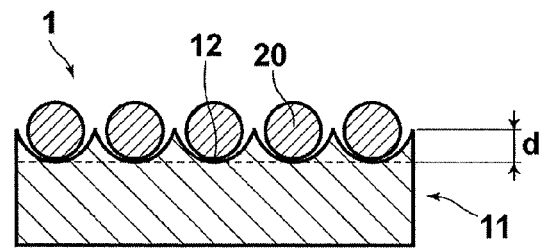
Figure 3A:
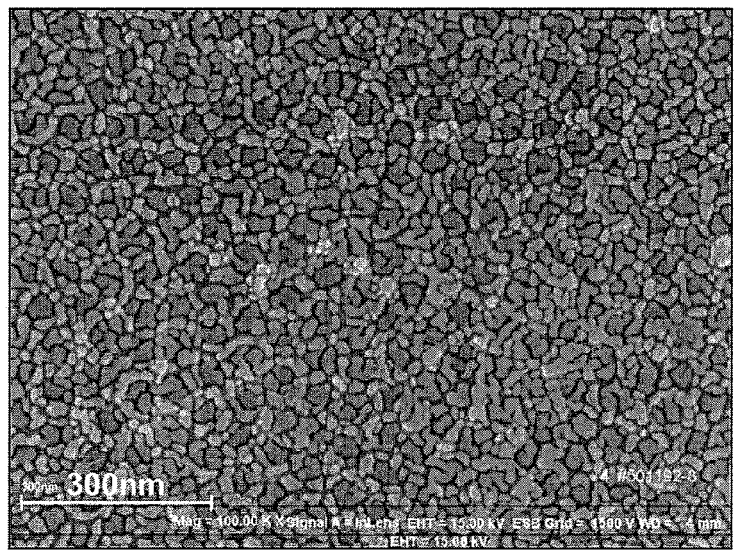
FIG. 3A is a SEM micrograph of a surface of a concrete example 1 before annealing.
Figure 3B:
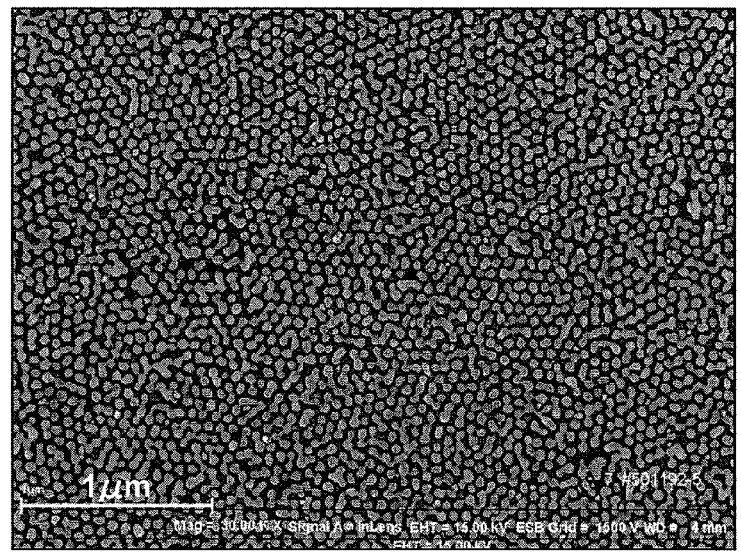
FIG. 3B is a SEM micrograph of the surface of the concrete example 1 after annealing.
Figure 4A:
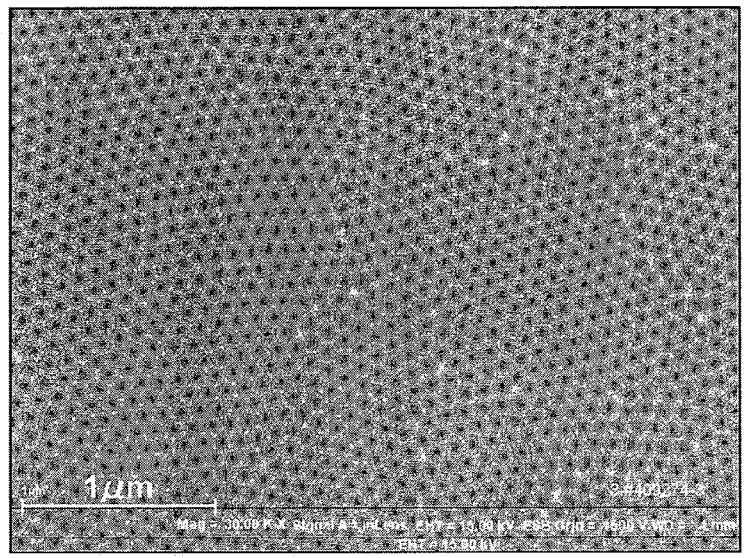
FIG. 4A is a SEM micrograph of a surface of a concrete example 2 before annealing.
Figure 4B:
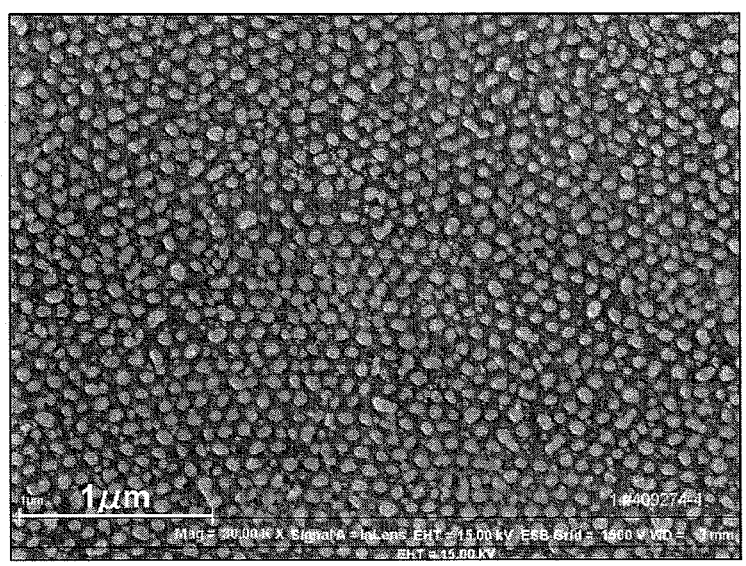
FIG. 4B is a SEM micrograph of the surface of the concrete example 2 after annealing.
Figure 5:
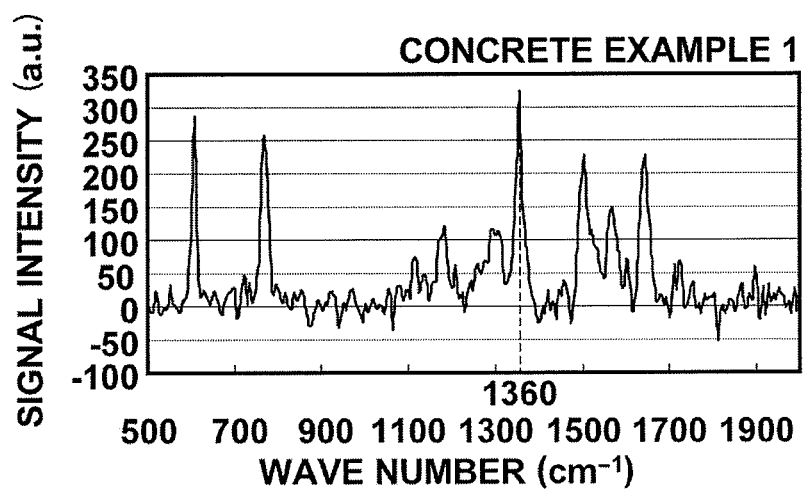
FIG. 5 is a graph indicating a Raman spectrum of the concrete example 1.
Figure 6:
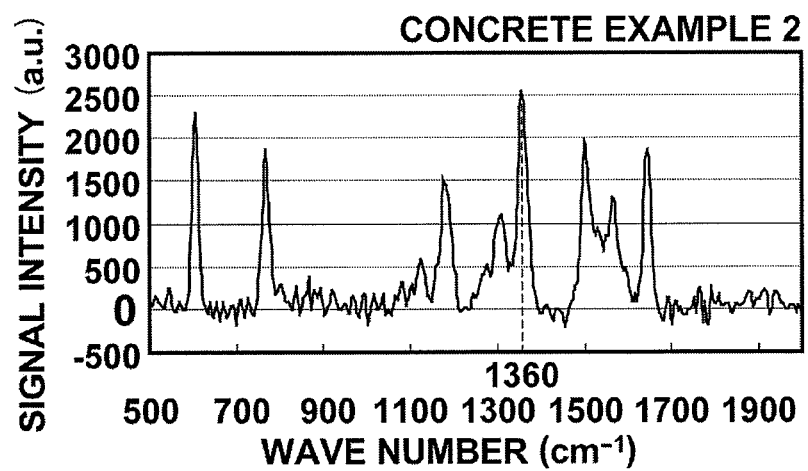
FIG. 6 is a graph indicating a Raman spectrum of the concrete example 2.

| EXPLANATION OF THE REFERENCE NUMERALS | |
|---|---|
| 1 | microstructured body |
| 10 | metal body |
| 11 | metal substrate |
| 12 | dimples |
| 30 | alumina layer |
| 20 | metal particles |
| 21 | metal film |

-continued

| | EXPLANATION OF THE REFERENCE NUMERALS |
|---|---|
| d | depths of the dimples |
| dm | thickness of the metal film |
| P | pitch of the dimples |

The invention claimed is:

1. A process for producing a microstructured body in which metal particles are arranged on a metal substrate, comprising the steps of:
   (A) preparing said metal substrate with a surface having a structure of protrusions and depressions;
   (B) forming on said surface of the metal substrate a metal film containing as a main component a metal which is different from a constituent metal of the metal substrate; and
   (C) annealing of said metal film so that a constituent metal of the metal film is coagulated into particles
   wherein the metal film is formed directly on the surface of the metal substrate.

2. A process according to claim 1, wherein said annealing in step (C) is performed at a temperature equal to or higher than a melting point of said metal film and lower than a melting point of said metal substrate.

3. A process according to claim 1, wherein said metal film has a thickness greater than depths of said depressions.

4. A microstructured body produced by said process according to claim 1.

5. A microstructured body according to claim 4, wherein said depressions have approximately identical shapes in a plan view, and are approximately regularly arranged in said structure.

6. A microstructured body according to claim 4, wherein an average pitch between said depressions does not exceed 400 nm.

7. A microstructured body according to claim 4, wherein said metal substrate is produced by anodizing a portion of a metal body so as to produce a metal-oxide layer and removing the metal-oxide layer from the metal body so as to leave an unanodized portion of the metal body.

8. A sensor device having a surface with which a specimen is to be arranged in contact, and outputting outgoing light with a physical property which is different according to the specimen and is to be detected when light for measurement is injected into the specimen, wherein said sensor device comprises said microstructured body according to claim 4.

9. A sensor device according to claim 8, sensing said specimen by use of localized plasmon resonance which occurs at surfaces of said metal particles.

10. A Raman spectrometry device having a surface with which a specimen is to be arranged in contact, and detecting Raman scattered light corresponding to light for measurement when the light for measurement is injected into the specimen, wherein said Raman spectrometry device comprises said microstructured body according to claim 4.

* * * * *